United States Patent [19]

Stormbom et al.

[11] Patent Number: 5,644,080
[45] Date of Patent: Jul. 1, 1997

[54] METHOD OF MEASURING DEWPOINT OR GAS CONCENTRATION AND APPARATUS FOR PREDICTION OF ICING

[75] Inventors: Lars Stormbom; Matti Lyyra, both of Vantaa, Finland

[73] Assignee: Vaisala Oy, Helsinki, Finland

[21] Appl. No.: 421,605

[22] Filed: Apr. 13, 1995

[30] Foreign Application Priority Data

Apr. 15, 1994 [FI] Finland .................................. 941746
Nov. 16, 1994 [FI] Finland .................................. 945385

[51] Int. Cl.$^6$ .............................. G01N 25/06; G01W 1/02
[52] U.S. Cl. ................................ 73/335.05; 73/170.26
[58] Field of Search ............................... 73/29.01, 29.02, 73/29.05, 335.02, 335.04, 335.05, 335.03, 170.26

[56] References Cited

U.S. PATENT DOCUMENTS

| | | | |
|---|---|---|---|
| 3,287,974 | 11/1966 | Ciemochowski | 73/335.04 X |
| 4,373,392 | 2/1983 | Nagamoto | 73/335.03 |
| 4,723,439 | 2/1988 | Asakura et al. | 73/335.05 X |
| 4,793,181 | 12/1988 | Djorup | 73/29.02 X |
| 4,793,182 | 12/1988 | Djorup | 73/29.01 X |
| 5,050,434 | 9/1991 | Demisch | 73/29.95 X |
| 5,296,819 | 3/1994 | Kuroiwa et al. | 73/335.04 X |
| 5,365,784 | 11/1994 | Morrissey | 73/335.05 X |

FOREIGN PATENT DOCUMENTS

| | | |
|---|---|---|
| 0262342 | 8/1987 | European Pat. Off. . |
| 349866 | 8/1970 | Sweden . |

*Primary Examiner*—Michael Brock
*Attorney, Agent, or Firm*—Birch, Stewart, Kolasch & Birch, LLP

[57] ABSTRACT

The invention relates to an indirect measurement method of dewpoint or gas concentration and an apparatus suited for prediction of icing. The method is based on measuring the relative concentration of the gas directly and simultaneously measuring the temperature of the element (3) measuring the relative concentration of the gas. According to the invention, the temperature of the relative value measuring element (3) is shifted so as to bring the operation of the measuring element to a measurement range of maximally high sensitivity.

3 Claims, 3 Drawing Sheets

METHOD OF MEASURING DEWPOINT OR GAS CONCENTRATION AND APPARATUS FOR PREDICTION OF ICING

FIELD OF THE INVENTION

The invention relates to a method for measuring dewpoint or gas concentration. The invention also concerns an apparatus for the prediction of icing.

DESCRIPTION OF THE PRIOR ART

In the prior art, the measurement of dewpoint or gas concentration is implemented in different ways. A traditional method of dewpoint measurement is to cool a suitable surface down to the occurrence of dew, detect the instant of dew occurrence and then measure the temperature corresponding to the time of the first occurrence of dew deposition. Conventionally, the surface for dew detection is a mirror surface and optical detection is used to monitor dew on such a mirror surface. Dew is detected optically from, e.g., the attenuation of light reflected from said mirror surface.

Other nonoptical methods employed in the art for dewpoint detection include capacitive methods and methods based on measuring the attenuation of a surface acoustic wave launched along the dew surface, whereby the dew surface forms a part of an electrical measurement circuit.

The above-described methods give a direct indication of the dewpoint temperature. The attainable accuracy is determined by the accuracies of dewpoint detection and surface temperature measurement.

The above-described methods are hampered by several disadvantages. For instance, contamination of the dew measurement surface causes error even if the countermeasures to contamination are attempted by way of cyclic measurement and automatic cleaning of dew surface. Notwithstanding such countermeasures, short maintenance intervals required under process conditions curtail the use of such apparatuses. Particularly, a measurement error source which is difficult to detect is caused by the deposition of a salt layer on the dew detector surface.

Under conditions of low partial pressure and slow evaporation of a deposited ice-water layer, the response time becomes long (up to several minutes) at low dewpoint temperatures in particular. Similarly, if the detector is wetted under a rapid change in ambient conditions, the recovery time will become long.

Methods are also known in the art based on indirect measurement of dewpoint from the relative humidity and the temperature corresponding to the measured relative humidity. With regard to the above-mentioned direct measurement approaches, the indirect method offers such advantages as fast response, reduced rate of contamination and possibility of operation at elevated temperatures.

The indirect method is hampered by a relatively large error at low levels of relative humidity and the deleterious attack of chemicals on the sensitivity of sensors measuring relative humidity.

Equipment for prediction of icing are based on monitoring the temporal trend of temperature and measuring the relative humidity in the vicinity of temperature zero point. A problem hampering the performance of these sensors is that at high values of relative humidity the humidity sensor easily remains wetted and thus indicates 100% RH for a long period of time.

SUMMARY OF THE INVENTION

It is an object of the present invention to overcome the drawbacks of the above-described techniques and to achieve an entirely novel method of dewpoint measurement and apparatus for prediction of icing.

The invention is based on shifting the measurement range of the sensor in particular at low values of RH by means of external cooling of the sensor to measure high RH, and correspondingly, in the vicinity of the dewpoint, shifting the measurement range by means of external heating of the sensor to such a range which gives the highest measurement accuracy.

Correspondingly, the apparatus for prediction of icing is based on designing the apparatus to comprise two separate sensor units, of which the first sensor unit incorporates a humidity sensor and a temperature sensor, while the second unit to be placed at the actual point of measurement merely incorporates a temperature sensor, and the first sensor unit is heated to a temperature above the ambient temperature to avoid the wetting of the humidity sensor by condensation.

More specifically, the method according to the invention includes the steps of (1) measuring the temperature of an element with a first temperature measurement sensor, wherein the element is capable of directly measuring the relative concentration of a gas;

(2) adjusting the temperature of the element until the temperature is within a measuring range wherein the element operates with maximum sensitivity; and (3) measuring the relative concentration of the gas with the element.

Furthermore, the apparatus according to the (1) a humidity measurement means, having:
  (A) a humidity measuring means for generating a humidity signal;
  (B) a first temperature measuring means located in the vicinity of the humidity measuring means for generating a first temperature signal; and
  (C) heating means for heating the humidity measurement means to a temperature above ambient temperature;

(2) a second temperature measurement means for measuring a temperature of an object or environment for which the occurrence of icing is to be predicted and for generating a second temperature signal, separate from the humidity measurement means; and (3) computing means for generating an icing warning signal from the humidity signal and the first temperature signal.

The invention offers significant benefits.

The method according to the invention provides fast response, good accuracy also at low values of RH, has good tolerance to contamination and permits accurate dewpoint measurement also at high temperatures. As the sensor according to the invention, when employed under process conditions, is subjected to dew only during the sensitivity calibration step of the sensor, the contamination of the sensor is essentially lower than in prior-art measurement methods.

Correspondingly, the apparatus according to the invention provides effective prediction of icing and commencement of deicing operations. Thus, heating of areas subject to icing in high masts and satellite antennas can be switched on prior to the formation of ice, whereby the risk of falling aggregations of ice can be avoided. Road maintenance authorities can minimize the amount of deicing chemicals consumption on the basis of more accurate ice reports. Small aircraft can move to warmer flight levels at the onset of an earlier icing warning. Further, damage to the blades of expensive generator turbines can be prevented with the help of the apparatus according to the invention.

In the following, the invention will be examined in more detail by means of exemplifying embodiments with reference to the attached drawings, in which:

DESCRIPTION OF THE PREFERRED EMBODIMENTS

Figure 1:
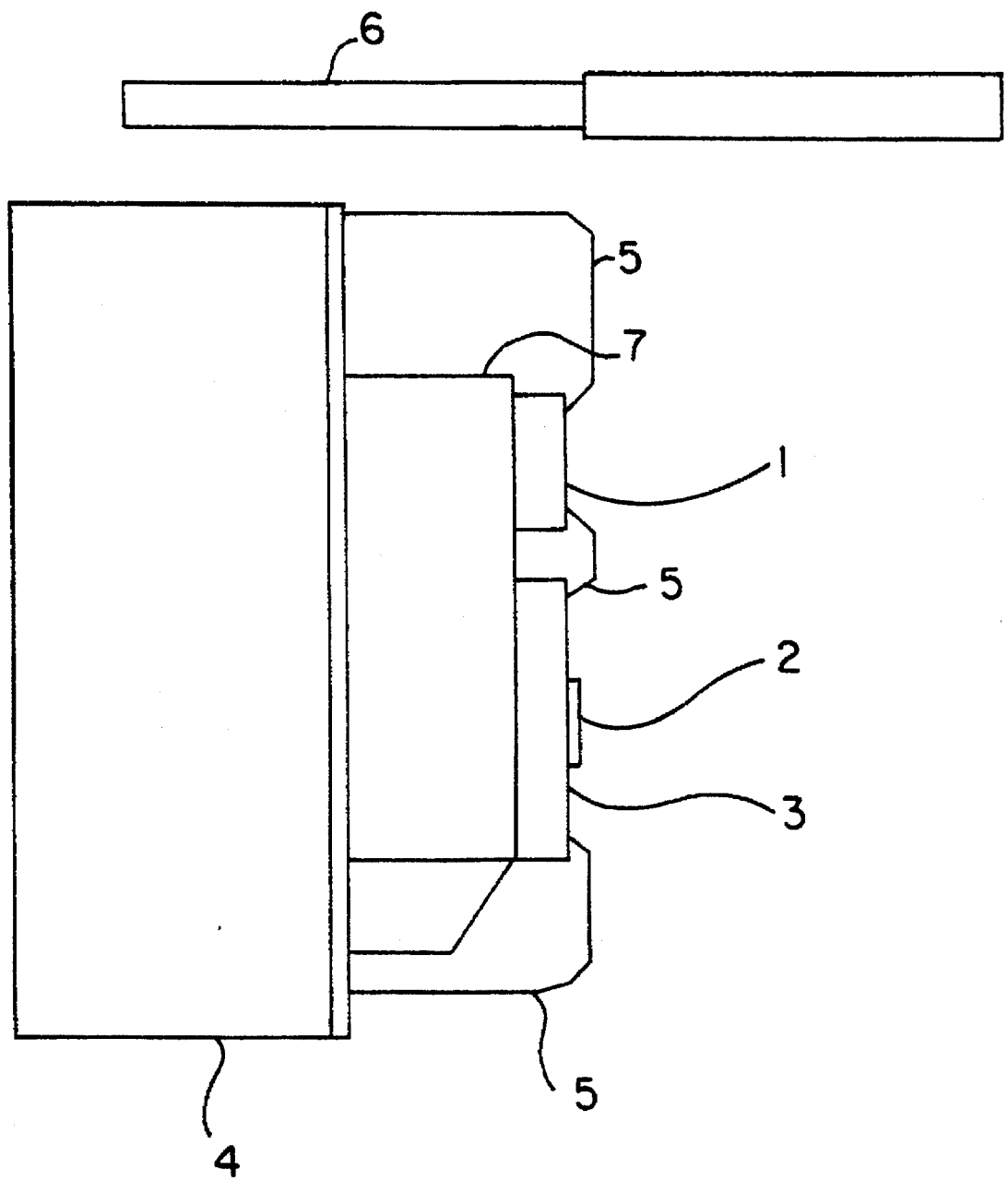
FIG. 1 is a basic diagram of a dewpoint measurement apparatus suited to implement the method according to the invention.

With reference to FIG. 1, the sensor assembly comprises a heater/cooler element (such as a Peltier element) 7 with a thin-film humidity sensor element 3 placed thereon having integrated to the outer surface electrode of the sensor an extremely miniature size heater resistor 2 which in the present embodiment is used as the dewpoint sensor. Additionally, the assembly is complemented with two temperature sensors 6 and 1. The external temperature sensor 6 measures the ambient temperature, while the internal temperature sensor 1 measures the temperature of the humidity sensor 3. The sensor construction is protected with moisture barriers 5 which seal the heater/cooler (such as a Peltier) element 7 against the fumes of the measured process. The humidity sensor 3 is of a type capable of delivering an output signal linearly proportional to the relative concentration of the measured gas. In this context, the term relative concentration must be understood as the ratio of the measured concentration of the gas to the saturated concentration of the gas at the measurement temperature. Sensors particularly suited for measuring the relative concentration of a gas include capacitive humidity sensors based on polymer materials. Such sensors are commercially available under such trade names as, e.g., Humicap®.

The operating-temperature of the humidity sensor 3 is shifted with the help of heater/cooler element (such as a Peltier element) a element 7 to the optimum range of the sensor temperature, and the sensor temperature is measured with the help of a separate temperature sensor 1. The ambient (or process) dewpoint is computed from the measurement result of the relative humidity of the humidity sensor 3 and the measured temperature of the humidity sensor 3. When required, the ambient temperature is measured with the help of the separate temperature sensor 6 for the purpose of computing the relative humidity.

The calibration of the sensor can be performed in, e.g., the following manner:

The calibration measurement results of humidity and temperature sensors are fitted to a basic model employed for each sensor type. With regard to humidity sensor calibration, the procedure described below is used. The values of the constants (kn, TCn and Dn) given below are specific for each sensor type, whereby they are dependent on the outer dimensions and materials of the sensor.

| | |
|---|---|
| Capacitance calibration: where | $C = C_0 + C_1 * U_{rh}$, $C_0$ and $C_1$ are calibration coefficients, $U_{rh}$ is the output voltage of the capacitance-to-voltage converter. |
| Humidity computation model: where | $C' = (C/C_{dry} - 1)*g$ $C_{dry} = 47$ $g = 1$ $C'' = C' + t*(k1 + t*(k3 + t*k4))$ |
| where | $t = T-25$ $k1 = -1.0218E-05$ $k2 = 1.32355E-06$ $k3 = -3.47684E-09$ $k4 = -6.34172E-12$ |
| $tc = Tc0 + T1*(Tc1 + T*(Tc2 + T*(Tc3 + T*(Tc4 + T*Tc5))))$ where | $T$ = temperature $Tc0 = 1.039304524$ $Tc1 = -2.56636E-03$ $Tc2 = 5.34072E-05$ $Tc3 = -4.93441E-07$ $Tc4 = 5.05655E-09$ $Tc5 = -1.12871E-11$ $C''' = 1 + C''*tc$ |
| $Rh = D0 + C'''*(D1 + C'''*(D2 + C'''*D3))$ where | $D0 = 6948.3$ $D1 = -19190.96$ $D2 = 17309.86$ $D3 = -5067.12$ |

Zero-point calibration is made under nitrogen flow and at room temperature.

Sensitivity calibration is performed at room temperature in a saturated-salt-solution-based humidity calibration cell capable of providing a relative humidity in the order of 90–98% RH. The temperature of the humidity sensor is not controlled, only the relative humidity is measured and the sensor output signal is corrected on the basis of the temperature difference between the saturated salt solution and the humidity sensor. The sensor linearity is calibrated in the humidity cell at certain intermediate points and, when necessary, the values of the coefficients D0–D3 are altered.

Calibration of temperature sensors is performed in two phases. First, both sensor inputs are calibrated with the help of a sensor simulator, after which the linear correction is performed in a temperature chamber using at least two different temperatures.

The individual temperature dependence of humidity sensors is calibrated in the humidity cell at room temperature utilizing the temperature control of the sensor.

Temperature dependence of the sensor zero point is calibrated at 0% RH in nitrogen flow, while the sensitivity calibration is performed at high humidity levels in the 60–95% RH range.

According to the invention, the temperature of the humidity sensor is controlled such that the sensor is brought to operate in its optimum range which for the above-mentioned polymer-based capacitive humidity sensor is in the order of 60–80% RH. Hence, if the process RH is in the 80–100% RH range, the sensor is typically heated so as to make it operate in the 60–80% RH range.

Correspondingly, if the RH is in the 0–60% RH range, the sensor is cooled so as to make it operate in the 60–80% RH range, or as close as possible to this range.

From the measurement results of the RH sensor and the temperature, the process gas partial pressure Pw and dewpoint Td are computed as follows:

$$P_w = A \cdot \frac{RHa}{100} \cdot 10^{[m - \frac{Trh}{Trh+Ta}]}$$

$$Td = \frac{Tp}{\left[\frac{m}{(^{10}\log(Pw/A))} - 1\right]}$$

and when required, the relative humidity of the process can be computed:

$$Rhp = Rha \cdot 10^{[m(\frac{Trh}{Trh-Ta} - \frac{Tp}{Tp+Ta})]}$$

where

Rhp=relative humidity in process
Rha=measured relative humidity
m=7.33354
Tp=process temperature
Trh=humidity sensor temperature
Ta=237.3° C.
A=6.1078

Hysteresis and dependence on chemicals are eliminated in the following manner: when the humidity level of the process is above 50% RH, the sensitivity of the humidity sensor is calibrated automatically approximately once a day by lowering the detector temperature until the 100% RH point is detected by the humidity sensor.

The measurement speed is determined by the response time of the humidity sensor. The rate of temperature control and recovery from wetting have no effect on the measurement speed.

The measurement range of relative humidity can be extended by lowering the operating temperature of the humidity sensor. The final accuracy of measurement is determined by the measurement accuracies of the relative humidity sensor and its operating temperature sensing.

Although the preferred embodiment of the invention relates to the measurement of the dewpoint of water, the invention may also be employed in the concentration measurement of other condensible gases (e.g., solvents).

Figure 2:
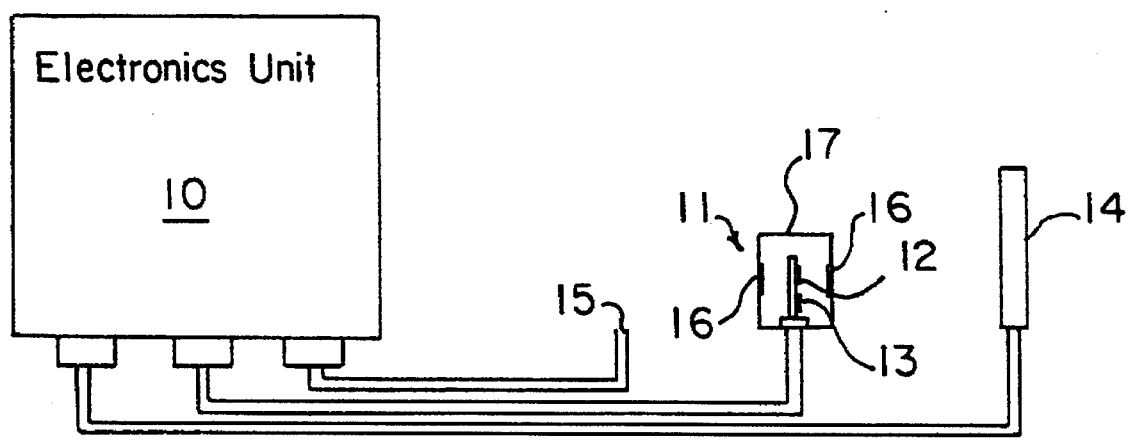
FIG. 2 is a basic diagram of an icing early-warning apparatus according to the invention.

With reference to FIG. 2, the apparatus according to the invention for prediction of icing is configured about an electronics unit 10. The apparatus comprises a first sensor unit 11 and a second sensor unit 14 connected the electronics unit 10. The first sensor unit 11 incorporates a humidity sensor 12 and a temperature sensor 13.

Accordingly, the first sensor unit can also be called the humidity measurement unit. Besides these, the humidity measurement unit 11 includes a heater element 16 for heating the sensor housing 17 to a temperature above the ambient temperature. The heater element 16 is controlled by means of the electronics unit 10 by, e.g., feeding the resistor 16 acting as the heater element with a constant power. Typically, elevating the operating temperature of the first sensor unit 11 by two kelvins above the ambient temperature is sufficient to keep the humidity sensor 12 dry. The temperature of the measured object proper (air temperature, antenna mast, aircraft wing, turbine, satellite antenna, etc.) is measured by means of the second sensor unit 14. The first sensor unit 11 and the second sensor unit 14 are generally located relatively far apart from each other. A warning signal reporting a possible icing condition is obtained from output 15 of the electronics unit 10.

Figure 3:
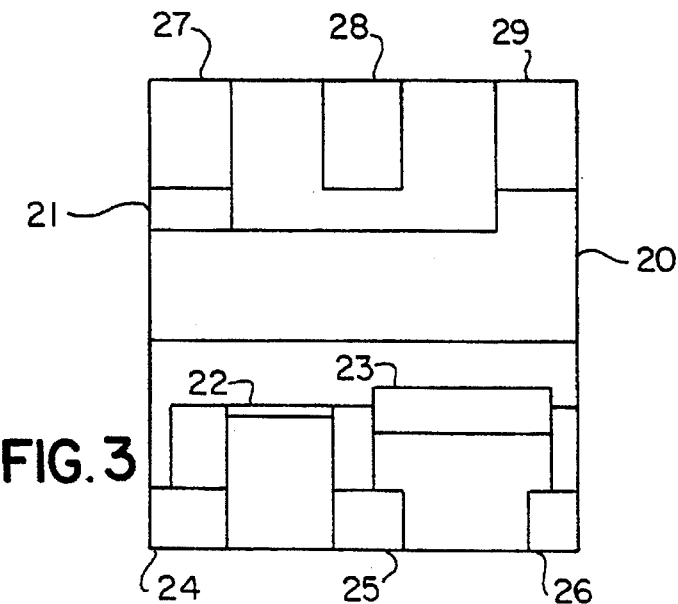
FIG. 3 is a diagram of the sensor construction employed in the apparatus according to the invention.

With reference to FIG. 3, a typical humidity sensor element of the sensor construction according to the invention is formed by a capacitive relative humidity sensor comprising contact areas 27, 28 and 29, and planar electrodes 21 and 20 of the sensing capacitor. A dielectric layer of suitable polymer is provided between the electrodes 20 and 21, exhibiting a change in its dielectric constant as a function of humidity. The humidity measurement unit shown in the diagram can be, e.g., similar to the sensor unit 12 illustrated in FIG. 2. Resistor elements 22 and 23 are integrated onto the same substrate with their respective contact areas 24, 25 and 26. The areas of the resistor elements 22 and 23 are designed to differ from each other in their thermal response such that when a similar voltage pulse is applied over the resistor elements, the smaller element 22 of the resistor elements will be dried by the applied heating effect if the element is wetted. However, the surface temperature of the larger resistor element 23 will not be elevated sufficiently to evaporate the condensate by the heating effect of the same voltage pulse. The material of the resistor elements 22 and 23 is chosen to exhibit the highest possible dependence of resistance on the temperature.

Figure 4:
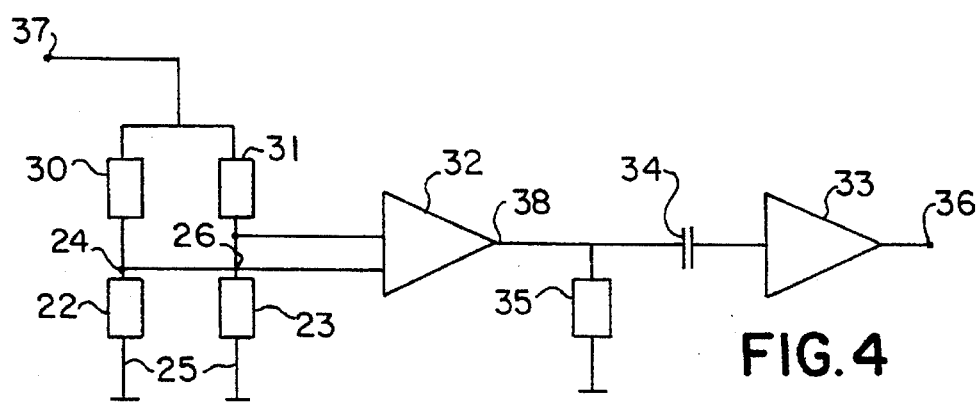
FIG. 4 is a circuit diagram of the dewpoint detection scheme according to the invention.

With reference to FIG. 4, the resistor elements 22 and 23 are connected in a bridge configuration with auxiliary resistors 30 and 31, and a voltage pulse is applied to point 37 of the bridge. The potential difference between points 24 and 26 of the bridge is amplified with the help of a differential amplifier 32 and a voltage signal is obtained from the amplifier output 38. The signal obtained from a derivator circuit formed by a resistor 35 and a capacitor 34 is amplified with the help of an amplifier 33, and the amplifier output signal is obtained at point 36.

Figure 5:
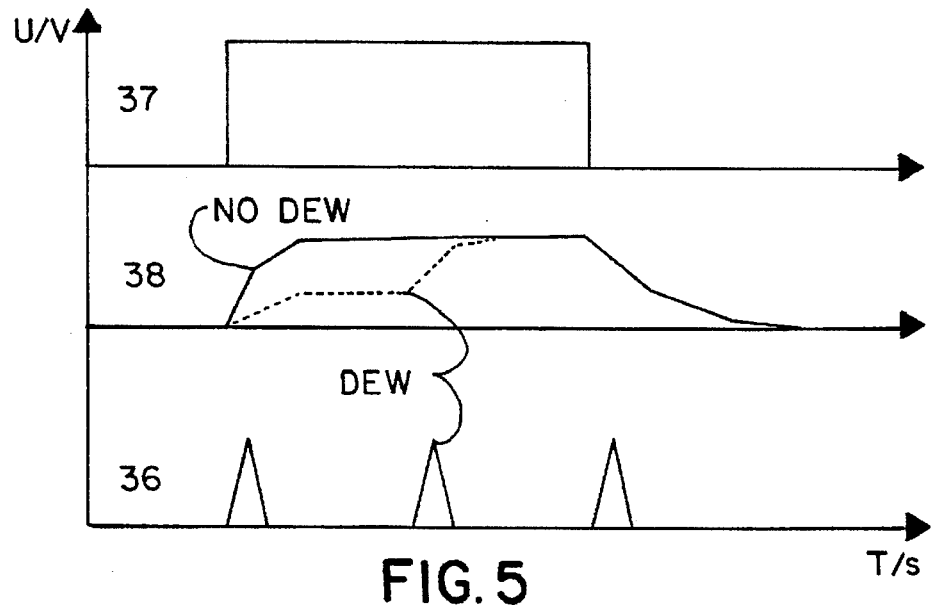
FIG. 5 is a graph illustrating the mutual temporal dependence of the signals of the circuit shown in FIG. 4.

With reference to FIG. 5, the signals of points 37, 38 and 36 of FIG. 4 are plotted on the same time scale. According to the uppermost curve, a voltage pulse is applied to the resistor bridge that generates the signals depicted by the centermost curve at the point 38. The situation plotted by the continuous line corresponds to the situation without condensation, while the case illustrated by the dashed line represents a situation where the sensor surface has a condensate layer. In the case of no condensation, the output signal of the differential amplifier 32 changes monotonously as a result of the different temperatures of the resistors of different sizes and the different resistances of the resistors. As shown by the lowermost curve, a voltage spike is obtained from the point 36 only in a transient situation. In the case of no condensation, the transient spike is obtained only at the leading and trailing edges of the applied voltage pulse. In the opposite case of the sensor wetted by the condensate, the drying of the smaller resistor 22 causes a rapid increase in its resistance thus causing a transient spike at the point 38. The transient signal further causes a condensation-indicating additional spike at the output 36, and hence, the wetting of the sensor can be positively detected by two independent methods: the relative humidity sensor 20, 21 and the resistance measurement.

Advantageously, the above-described configuration is complemented with a heater/cooler element (such as a Peltier element) element 7, e.g., as shown in FIG. 1, whereby said element makes it possible to cool the humidity sensor part of the sensor unit to the dew-point for calibration purposes. At this temperature the dewpoint can be detected by resistance sensing and thus the point of 100% RH can be determined with a high accuracy for the capacitive humidity sensor 20, 21. As the sensor construction also includes the temperature sensor 13 shown in FIG. 2, the sensitivity of the humidity sensor can be determined from the calibrated dewpoint and the temperature information. If the relative humidity is high (RH greater than 85%), the calibration step can be carried out daily. At lower humidity values (in the range of 60–85% RH), weekly calibration is sufficient.

Furthermore, the sensitivity change of the polymer-based humidity sensor under the effect of solvents can be eliminated by controlling the heater element 7 adapted to the humidity sensor as shown in FIG. 1 such that, e.g., the temperature of the polymer-based dielectric of the measuring capacitor is temporarily elevated by at least 100 K above the ambient temperature. Such a temperature shock expels absorbed solvents from the dielectric material and restores the properties of the humidity sensor.

We claim:

1. An apparatus for predicting the occurrence of icing, comprising:
   (1) a humidity measurement means, further comprising:
      (A) a humidity measuring means for generating a humidity signal;
      (B) a first temperature measuring means located in the vicinity of said humidity measuring means for generating a first temperature signal;
      (C) heating means for heating said humidity measurement means to a temperature above ambient temperature; and
      (D) cooling means for cooling said humidity measurement means to dewpoint;
   (2) two resistor means having different thermal responses, located in the vicinity of said humidity measurement means, for detecting the dewpoint when a pulsed signal is applied over said resistor means;
   (3) a second temperature measurement means for measuring a temperature of an object or environment for which the occurrence of icing is to be predicted, separate from said humidity measurement means; and
   (4) computing means for generating an icing warning signal from said humidity signal and said first temperature signal.

2. The apparatus according to claim 1, wherein said heating means and said cooling means constitute a single heating/cooling means.

3. The apparatus according to claim 2, wherein said heating/cooling means is a Peltier element.

* * * * *